(12) United States Patent
Fu et al.

(10) Patent No.: US 9,841,423 B2
(45) Date of Patent: Dec. 12, 2017

(54) **METHODS FOR DIAGNOSING AND TREATING *HELICOBACTER PYLORI* INFECTION**

(71) Applicant: National Tsing Hua University, Hsinchu (TW)

(72) Inventors: Hua-Wen Fu, Hsinchu (TW); Ting-Yu Kuo, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/985,413

(22) Filed: Dec. 31, 2015

(65) Prior Publication Data
US 2017/0082621 A1 Mar. 23, 2017

(30) Foreign Application Priority Data
Sep. 21, 2015 (TW) .............................. 104131171 A

(51) Int. Cl.
| | | |
|---|---|---|
| *A61K 39/40* | (2006.01) | |
| *C07K 16/12* | (2006.01) | |
| *G01N 33/569* | (2006.01) | |
| *G01N 33/577* | (2006.01) | |
| *A61K 39/00* | (2006.01) | |

(52) U.S. Cl.
CPC ........ *G01N 33/56911* (2013.01); *A61K 39/40* (2013.01); *C07K 16/121* (2013.01); *G01N 33/577* (2013.01); *A61K 2039/505* (2013.01); *C07K 2317/34* (2013.01); *C07K 2317/76* (2013.01); *G01N 2333/205* (2013.01)

(58) Field of Classification Search
None
See application file for complete search history.

(56) References Cited

FOREIGN PATENT DOCUMENTS

WO    WO 2013/143026    * 10/2013

OTHER PUBLICATIONS

Kimura et al. Science; Jun. 2, 1995; 268:1362-1365.*
Ting-Yu Kuo et al., "A commercial monoclonal antibody X is a new tool for detecting Helicobacter pylori neutrophil-activating protein", Hsinchu, Taiwan, Mar. 21-22, 2015.
Ting-Yu Kuo et al., "A commercial monoclonal antibody X is a new tool for detecting Helicobacter pylori neutrophil-activating protein", Hsinchu, Taiwan, Apr. 11, 2015.
Ting-Yu Kuo et al., "A commercial monoclonal antibody X acts as a blocking antibody to Helicobacter pylori neutrophil-activating protein", Hsinchu, Taiwan, Jun. 26-29, 2015.
Hua-Wen Fu, "Helicobacter pylori neutrophil-activating protein: from virulence factors to potential therapeutic targets and diagnostic biomarkers", Hsinchu, Taiwan, Nov. 17, 2015.
Ting-Yu Kuo et al., "A commercial monoclonal antibody X is a new tool for detecting Helicobacter pylori neutrophil-activating protein", Taipei, Taiwan, Mar. 21-22, 2015.
Ting-Yu Kuo et al., "A commercial monoclonal antibody X is a new tool for detecting Helicobacter pylori neutrophil-activating protein", Taipei, Taiwan, Apr. 11, 2015.
Ting-Yu Kuo et al., "A commercial monoclonal antibody X acts as a blocking antibody to Helicobacter pylori neutrophil-activating protein", Hsinchu, Taiwan, Jun. 2, 2015.
Ting-Yu Kuo et al., "A commercial monoclonal antibody X acts as a blocking antibody to Helicobacter pylori neutrophil-activating protein", Taipei, Taiwan, Jun. 26-29, 2015.
Hua-Wen Fu, "Helicobacter pylori neutrophil-activating protein: from virulence factors to potential therapeutic targets and diagnostic biomarkers", Singapore, Nov. 17, 2015.
Doyle J. Evans, Jr. et al., "Characterization of a Helicobacter pylori neutrophil-activating protein", Infection and Immunity, Jun. 1995, p. 2213-2220.
Barbara Satin et al., "The neutrophil-activating protein (HP-NAP) of Helicobacter pylori is a protective antigen and a major virulence factor", J. Exp. Med., May 1, 2000, p. 1467-1476.
Chung-An Wang et al., "Helicobacter pylori neutrophil-activating protein promotes myeloperoxidase release from human neutrophils", Biochemical and Biophysical Research Communications, 377 (2008) 52-56.

* cited by examiner

*Primary Examiner* — Oluwatosin Ogunbiyi
(74) *Attorney, Agent, or Firm* — WPAT, P.C., Intellectual Property Attorneys; Anthony King

(57) ABSTRACT

The present invention provides methods for diagnosing and treating *Helicobacter pylori* infection by using a monoclonal antibody to detect *Helicobacter pylori* neutrophil-activating protein (HP-NAP) and inhibit the activity thereof. The monoclonal antibody is an ANTI-FLAG antibody that binds to a specific epitope on HP-NAP for the detection of HP-NAP in its native form or denatured form. Furthermore, the present invention uses the ANTI-FLAG antibody to block HP-NAP-induced production of reactive oxygen species by human neutrophils. Thus, the present invention can be applied in clinical diagnosis of *Helicobacter pylori* infection as well as treatment of the infection via inhibiting *Helicobacter pylori*-induced inflammation.

11 Claims, 12 Drawing Sheets

FIG. 7

| | | 10 | 20 | 30 | 40 | 50 | 60 | 70 | 80 | |
|---|---|---|---|---|---|---|---|---|---|---|
| 26695 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:19) |
| NCTC11639 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:20) |
| NCTC11637 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:21) |
| J99 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:22) |
| OK310 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:23) |
| 51 | | MKTFEILKHL | QADAIVLFMK | VHNFHWNVKG | TDFFNVHKAT | EEIYEGFADM | FDDLAERIVQ | LGHHPIVTLS | EAIKLTRVKE | (SEQ ID NO:24) |
| G27 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:25) |
| Puno135 | | MKTFEILKHL | QADAIVLFMK | VHNFHWNVKG | TDFFNVHKAT | EEIYEEFADM | FDDLAERIAQ | LGHHPIVTLS | EAIKLTRVKE | (SEQ ID NO:26) |
| NY40 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:27) |
| P79 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:28) |
| Gambia94/24 | | MKTFEILKHL | QADAIVLFMK | VHNFHWNVKG | TDFFNVHKAT | EEIYEGFADM | FDDLAERIVQ | LGHHPIVTLS | EAIKLTRVKE | (SEQ ID NO:29) |
| SouthAfrica7 | | MKTFEILKHL | QADAIVLFMK | VHNFHWNVKG | TDFFNVHKAT | EEIYEEFADM | FDDLAERIVQ | LGHHPIVTLS | EAIKLTRVKE | (SEQ ID NO:30) |
| Consistency | | ******** | ****** | ****** | ****** | **:* | *****: | ******** | ******** | |

| | | 90 | 100 | 110 | 120 | 130 | 140 | |
|---|---|---|---|---|---|---|---|---|
| 26695 | | LTKCSFHSKD | YLEKIFTELS | NTAEKEGDRV | TVTTADDQLA | KLQRSIWMLQ | AELA | |
| NCTC11639 | | LTKCSFHSKD | HLEKIFTELS | NTAEKEGDRV | TVTTADDQLA | KLQRSIWMLQ | AELA | |
| NCTC11637 | | LTKCSFHSKD | HLEKIFTELS | NTAEKEGDRV | TVTTADDQLA | KLQRSIWMLE | AELA | |
| J99 | | LTKCSFHSKD | HLEKIFTELS | NTAEKEGDRV | TVTTADDQLA | KLQRSIWMLE | AELA | |
| OK310 | | LTKCSFHSKD | HLEKIFTELS | NTAEKEGDRV | TVTTADDQLA | KLQRSIWMLE | AELA | |
| 51 | | LTKCSFHSKD | HLEKIFTELS | NTAEKEGDRV | TVTTADDQLA | KLQRSIWMLE | AELA | |
| G27 | | LTKCSFHSKD | HLEKIFTELS | NTAEKEGDRV | TVTTADDQLA | KLQRSIWMLE | AELA | |
| Puno135 | | LTKCSFHSKD | HLEKIFTELS | NTAEKEGDRV | TVTTADDQLA | KLQRSIWMLE | AELA | |
| NY40 | | LTKCSFHSKD | HLEKIFTELS | NTAEKEGDRV | TVTTADDQLA | KLQRSIWMLE | AELA | |
| P79 | | LTKCSFHSKD | HLEKIFTELS | NTAEKEGDRV | TVTTADDQLA | KLQRSIWMLE | AELA | |
| Gambia94/24 | | LTKCSFHSKD | YLEKIFTELS | NTAEKEGDRV | TVTTADDQLA | KLQRSIWMLE | AELA | |
| SouthAfrica7 | | LTKCSFHSKD | HLEKIFTELS | NTAEKEDDRV | TVTTADDRLA | KLQRSIWMLE | AELA | |
| Consistency | | ******** | :***** | ****: | ******: | **********:* | **** | |

HP-NAP$_{R77-E116}$

METHODS FOR DIAGNOSING AND TREATING *HELICOBACTER PYLORI* INFECTION

CROSS-REFERENCE TO RELATED APPLICATION

This application claims priority of Taiwan patent application No. 104131171, filed on Sep. 21, 2015, the content of which is incorporated herein in its entirety by reference.

BACKGROUND OF THE INVENTION

1. Field of the Invention

The present invention relates to methods for diagnosing and treating *Helicobacter pylori* infection, particularly relates to methods for detecting *Helicobacter pylori* neutrophil-activating protein (HP-NAP) and inhibiting the activity of HP-NAP by using an antibody.

2. The Prior Art

*Helicobacter pylori* (*H. pylori*) is a gram-negative, microaerophilic bacterium that may infect around one-third of the people in the world. According to epidemiology reports, more than ten million people are infected with *H. pylori* among healthy population in Taiwan. In a host, *H. pylori* colonizes the gastric mucosa of stomach and triggers inflammation. It is highly associated with the pathogenesis of acute and chronic gastritis, peptic ulcer, duodenitis, lymphoma, gastric adenocarcinoma and other gastric cancers. In 1994, World Health Organization (WHO) declared *H. pylori* as a Class I carcinogen. Thus, infection by *H. pylori* has become an essential public health issue.

The commonly used clinical tests for *H. pylori* infection include biopsy, gastroscopy, and urea breath test (UBT) with the use of carbon isotopes. Laboratory tests also include the gastric tissue culture and serological test. However, the gastric tissue culture may easily yield false positive or false negative results due to the operation process; the urea breath test is too expensive for developing countries. Although diagnosis by polymerase chain reaction (PCR) has been developed, this method is costly, time-consuming and not clinically applicable.

HP-NAP is a virulence factor produced by *H. pylori* strains. It is a dodecameric protein consisting of twelve identical subunits, each of which is a four-helix bundle with a molecular weight of 17 kDa. HP-NAP induces production of reactive oxygen species (ROS) by neutrophils through the activation of a pertussis toxin (PTX)-sensitive G protein-coupled receptor (GPCR). It is also a ligand of Toll-like receptor 2 (TLR2), which is involved in HP-NAP-induced release of interleukin-6 (IL-6) in splenocytes. HP-NAP also stimulates neutrophils to produce myeloperoxidase, chemokines and pro-inflammatory cytokines and induces neutrophil chemotaxis and neutrophil-endothelial adhesion. In addition, HP-NAP is able to activate monocytes and mast cells. The inflammatory mediators produced by these innate immune cells upon *H. pylori* infection can lead to gastric mucosal damage.

As a result, HP-NAP may be a potential target for diagnosis and treatment of *H. pylori* infection because of its important role in the pathogenesis of diseases initiated by *H. pylori* infection. Since there is an urgent need for fast and accurate diagnosis of *H. pylori* infection, development of new detection methods based on detecting HP-NAP may be the solution.

SUMMARY OF THE INVENTION

One aspect of the present invention provides a method for diagnosing *Helicobacter pylori* infection in a subject, comprising the steps of: (a) providing a test sample from the subject; (b) contacting the test sample with an ANTI-FLAG antibody; and (c) detecting a binding of the ANTI-FLAG antibody of step (b) to HP-NAP produced by *H. pylori* in the test sample to determine the presence or absence of *H. pylori*; wherein *H. pylori* infection is diagnosed in the subject when the binding of the ANTI-FLAG antibody to the HP-NAP is detected.

In one embodiment of the present invention, the ANTI-FLAG antibody binds to an epitope on HP-NAP, and the epitope comprises an amino acid sequence of SEQ ID NO:2.

In another embodiment of the present invention, HP-NAP is in a native form or a denatured form.

For the method of the present invention, the test sample is selected from the group consisting of gastric fluid, intestinal fluid, blood, serum, urine, feces and combinations thereof. The ANTI-FLAG antibody is selected from the group consisting of an IgG/M2 monoclonal antibody, an IgG/6F7 monoclonal antibody and combinations thereof. The step (c) is selected from the group consisting of western-blotting, enzyme-linked immunosorbent assay, indirect immunofluorescence testing (IIFT), immunohistochemical staining, immunoprecipitation and combinations thereof.

Another aspect of the present invention provides a method for treating *Helicobacter pylori* infection in a subject, comprising administrating to the subject an effective amount of an ANTI-FLAG antibody, wherein the ANTI-FLAG antibody inhibits the activity of HP-NAP.

In one embodiment of the present invention, the ANTI-FLAG antibody further combines with an anti-inflammatory agent for treating *H. pylori* infection, wherein the anti-inflammatory agent is selected from the group consisting of glucocorticoids, corticosteroids, T-cell blockers, purine analogs, pyrimidine analogs, alkylating agents, antifolates, antibiotics, antibodies and combinations thereof. The ANTI-FLAG antibody is selected from the group consisting of an IgG/M2 monoclonal antibody, an IgG/6F7 monoclonal antibody and combinations thereof.

One further aspect of the present invention provides a device for detecting *Helicobacter pylori*, comprising an ANTI-FLAG antibody, wherein the ANTI-FLAG antibody specifically binds to HP-NAP.

One further aspect of the present invention provides a method for specific recognition of a protein having an amino acid sequence of SEQ ID NO:2, comprising contacting the protein with an antibody which recognizes SEQ ID NO:2. In one embodiment of the present invention, the protein is HP-NAP, and the antibody inhibits the activity of the HP-NAP.

The present invention is further explained in the following drawings and examples. It is understood that the examples given below do not, however, limit the scope of the invention, and it will be evident to those skilled in the art that modifications can be made without departing from the scope of the appended claims.

BRIEF DESCRIPTION OF THE DRAWINGS

FIG. 7 shows the amino acid sequence alignment of HP-NAP from *H. pylori* 26695 and eleven other *H. pylori* strains; the amino acid sequence alignment compares the amino acid sequences of SEQ ID NOs: 19-30.

DETAILED DESCRIPTION OF THE PREFERRED EMBODIMENT

Figure 1:
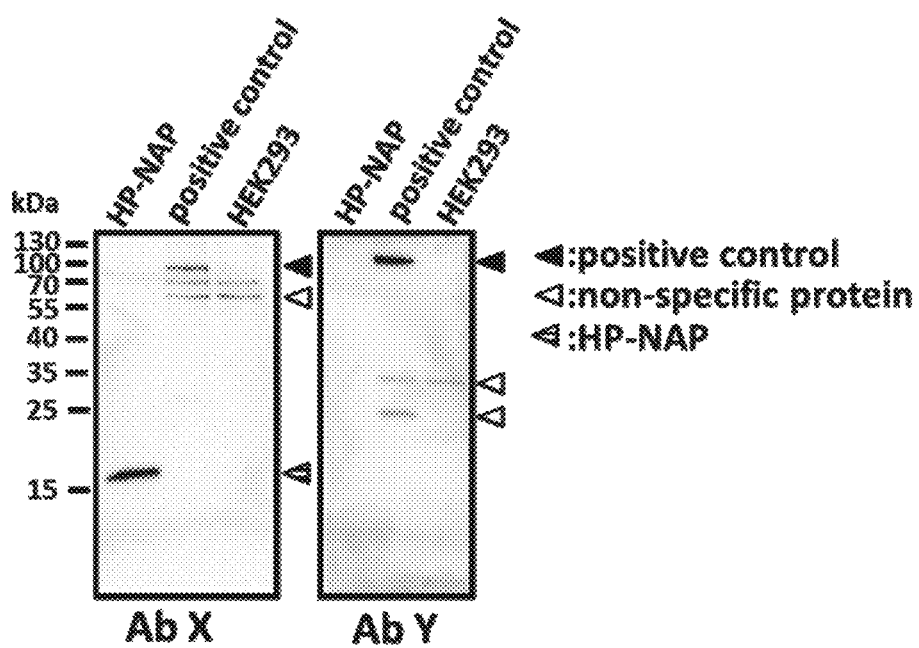
FIG. 1 shows detection of recombinant *Helicobacter pylori* neutrophil-activating protein (HP-NAP) in its denatured form by western-blot analysis using antibody X.

One embodiment of the present invention uses a commercial IgG/M2 monoclonal antibody, which is designated as antibody X. Another commercial IgG/M1 monoclonal antibody, designated as antibody Y, is used as a control.

By western-blot and enzyme linked immunosorbent assay (ELISA) analyses, the present invention shows a commercial antibody X can detect *Helicobacter pylori* neutrophil-activating protein (HP-NAP) in its native form or denatured form. In addition, single site-directed mutagenesis was carried out for epitope mapping on HP-NAP. To verify the capability of antibody X to detect HP-NAP from different *H. pylori* strains, western-blot and ELISA analyses were performed with HP-NAP mutants based on the results of amino acid sequence alignment. Furthermore, the present invention shows the antibody X can inhibit HP-NAP-induced production of reactive oxygen species (ROS) by human neutrophils.

Definition

The term "test sample" used in the present invention refers to any sample obtained from biological subjects including humans and non-human mammals. Such samples comprise, but not limited to, body fluid (e.g., blood, serum, plasma, urine, gastric fluid, intestinal fluid, cerebrospinal fluid, tears, saliva, lymph, dialysate, lavage fluid and other fluidic specimens), cells and tissues from living organisms. Test samples also include cells and their derived cell populations, cells in culture medium, cell fractions and supernatants. Test samples may also include fluids derived from organs or tissue cultures, a biopsy sample, a biopsy sample of tumor, a feces sample, fluids extracted from tissues, isolated solid tissues and tissue sections. Test samples also include samples that are treated in any process, for example, treatment with agents, homogenization, and enrichment for specific components (e.g., polynucleotides or peptides). Test samples also include stools and fractions of samples from patients.

The term "device" used in the present invention refers to any device used for analysis, in any forms and sizes and being made from any materials. The device comprises a detecting region for a test sample which might contain an analyte to pass through or be retained in. In the detecting region, an analyte, if present, interacts with a detecting agent, and the presence or absence of the analyte and/or its quantity is reported.

Materials and Methods
Cell Culture

Human embryonic kidney 293 (HEK 293, ATCC CRL-1573) cells were cultured in minimum essential medium with Earle's salts (Invitrogen), and supplemented with 10% fetal bovine serum in the presence of 100 units/ml penicillin and 50 µg/ml streptomycin at 37° C. under humidified atmosphere containing 5% CO$_2$.

Transfection and Lysis of HEK 293 Cells

HEK 293 cells were transfected with 4 µg of plasmid DNA encoding one common target protein of antibodies X and Y and 8 µl of Lipofectamine 2000 (Invitrogen) in 35 mm dishes according to the manufacturer's instructions (Invitrogen). To transfect cells in different formats, the amounts of Lipofectamine 2000 and DNA were scaled up in proportion to the relative surface area of the cultured dishes.

After 48 hours of post-transfection, the cells were scraped into 150 µl of 50 mM Tris-HCl, pH 7.4, with 250 mM NaCl, 1% Triton X-100, 1 mM phenylmethylsulfonyl fluoride (PMSF), 0.5 mM ethylenediaminetetraacetic acid (EDTA), 10 µg/ml aprotinin, and 1 mM Na$_3$VO$_4$. The cell suspension was sonicated thirty times with 50% amplitude and 0.5 cycle at 4° C. using an UP 50H ultrasonicator (Dr. Hielscher GmbH, Teltow, Germany) The insoluble material was removed by centrifugation. The supernatant was collected as the whole cell lysate.

*H. pylori* Strains and Culture Conditions

*H. pylori* strain 26695 (ATCC 700392), NCTC 11639 (ATCC 43629) and NCTC 11637 (ATCC 43504) were obtained from the Bioresource Collection and Research Center (BCRC, Taiwan). All strains were grown for 3 days under microaerophilic condition using GasPak EZ Container System Sachets (BD BBL; Sparks, Md., USA) and 100% humidity at 37° C. on trypticase soy agar (TSA) with 5% sheep blood (BD BBL). For expanding the culture, the *H. pylori* colonies from TSA plates were transferred into Brucella broth (BD BBL) with 10% horse serum (JRH Biosciences, Lenexa, Kans., USA) and then grown for 2 days. The cells were centrifuged at 6,000×g at 4° C. for 15 minutes to remove the supernatant and stored at −70° C.

Cloning of HP-NAP$_{R77-E116}$ into an *E. coli* Expression Vector Producing Maltose-Binding Protein (MBP) Fusion Protein The plasmid DNA pET42a-NAP encoding a nap gene from *H. pylori* strain 26695 [GenBank: AE000543.1, Gene: HP0243] was prepared as previously described (Wang et al., 2008). The DNA fragment coding for the polypeptide containing residues Arg77 to Glu116 of HP-NAP (HP-NAP$_{R77-E116}$) was amplified by polymerase chain reaction (PCR) from the plasmid pET42a-NAP using forward and reversed primers containing BamHI and HindIII sites, respectively. The forward primer is 5'-ATAAGGATCCCGT-GTTAAAGAAGAAACTAAAAC-3' (SEQ ID NO:3) and the reversed primer is 5'-TTAATAAGCTTTAAT-TCTTTTTCAGCGGTGTTAGAG-3' (SEQ ID NO:4). The PCR reaction was carried out with 10 ng plasmid DNA pET42a-NAP as template and KAPA HiFi PCR Kit (Kapa Biosystems, Inc.) in a Mastercycler Gradient 5331 (Eppendorf, Germany) An initial denaturing phase of 95° C. for 5 minutes was followed by 39 cycles of 98° C. for 20 seconds, 67° C. for 15 seconds, and 72° C. for 15 seconds. A final elongation phase of 72° C. for 2 minutes was also included. The amplified DNA fragments encoding HP-NAP$_{R77-E116}$ were then cloned into pJET1.2/blunt vectors using the CloneJET PCR Cloning Kit (Thermo Fisher Scientific Inc.). The resulting plasmid, designated as pJET1.2/blunt HP-NAP$_{R77-E116}$, was sequenced to confirm the correct DNA sequence of the insert. The DNA fragment encoding HP-NAP$_{R77-E116}$ was digested from pJET1.2/blunt HP-NAP$_{R77-E116}$ with BamHI and HindIII and then cloned into the pMAL c2g expression vector (New England Biolabs). The resulting plasmid was designated as pMAL c2g HP-NAP$_{R77-E116}$, which encodes a maltose-binding protein (MBP)-tagged HP-NAP$_{R77-E116}$ (MBP-HP-NAP$_{R77-E116}$).

Single Site-Directed Mutagenesis

Site-directed mutagenesis was carried out by a PCR-based method. An amount of 10 ng plasmid DNA pET42a-NAP, 1 μM mutagenesis primer pairs listed in Table 1, 200 μM deoxynucleoside triphosphates (dNTPs) and 3 units of high-fidelity PCR enzyme mix (Expand Long Template PCR System, Roche) were added into a PCR tube containing deionized water, giving a final volume of 25 μl. The PCR cycles were initiated at 95° C. for 10 minutes to denature the template DNA, followed by 12 amplification cycles. Each amplification cycle consisted of 95° C. for 1 minute, $T_{m\,no}$–5° C. for 1 minute and 72° C. for 6 minutes. The PCR cycles were finished with an additional annealing step at $T_{m\,pp}$–5° C. for 1 minute and an extension step at 72° C. for 30 minutes. The PCR products with the volume of 15 μl were treated with 5 units of Dpn I (New England Biolabs, NEB) at 37° C. for 2 hours. Then, 2 μl of each Dpn I-treated PCR reaction was analyzed by agarose gel electrophoresis. The above Dpn I-treated PCR products with a volume of 2 μl were transformed into E. coli DH5α (Invitrogen) competent cells by heat shock. The transformed cells were spread on a lysogeny broth (LB) plate containing 50 μg/ml kanamycin and incubated at 37° C. for 16 hours. A single colony was inoculated into LB containing 50 μg/ml kanamycin and shaken at 170 rpm at 37° C. for 16 hours, and the plasmid DNA was isolated. The plasmid DNA was treated with individual restriction enzyme for verifying the silent mutation. The plasmid was then sequenced with T7 promoter primer to confirm the correction of the coding sequences of HP-NAP mutants. The plasmids with desired mutations were transformed into E. coli BL21 (DE3) (Invitrogen) competent cells by heat shock.

TABLE 1

Primers used in single site-directed mutagenesis

| HP-NAP mutants | primers | sequence | $T_{m\,pp}$ (° C.)[a] | $T_{m\,no}$ (° C.)[b] |
|---|---|---|---|---|
| HP-NAP$_{E97GY101H}$ | Hp26695-NAP14415 + (E97GY101H) + XhoI+ | 5' ACAAACATCTCGAGAAAGAATTTAAAGAGCTCTCTAACACCG 3' (SEQ ID NO: 5) | 54 | 62 |
| | Hp26695-NAP14415 + (E97GY101H) + XhoI- | 5' TTCTTTCTCGAGATGTTTGTAGTCCCCTAGAATTTCTTTAAAGAT 3' (SEQ ID NO: 6) | 54 | 62 |
| HP-NAP$_{D98A}$ | Hp26695-NAP14418 + (K100A) + XhoI+ | 5' AAATTCTCGAGGCTTACAAATATCTAGAAAAAGAATTTAAAGAGC 3' (SEQ ID NO: 7) | 54 | 62 |
| | Hp26695-NAP14418 + (K100A) + XhoI- | 5' TTTGTAAGCCTCGAGAATTTCTTTAAAGATGTCTTTAGAGTGG 3' (SEQ ID NO: 8) | 54 | 62 |
| HP-NAP$_{Y99A}$ | Hp26695-NAP14421 + (Y99A) + XhoI+ | 5' ATTCTCGAGGACGCCAAATATCTAGAAAAAGAATTTAAAGAGC 3' (SEQ ID NO: 9) | 54 | 62 |
| | Hp26695-NAP14421 + (Y99A) + XhoI- | 5' TTTGGCGTCCTCGAGAATTTCTTTAAAGATGTCTTTAGAGTGG 3' (SEQ ID NO: 10) | 54 | 62 |
| HP-NAP$_{K100A}$ | Hp26695-NAP14424 + (K100A) + MluI+ | 5' AGGACTACGCGTATCTAGAAAAAGAATTTAAAGAGCTCTC 3' (SEQ ID NO: 11) | 50 | 60 |
| | Hp26695-NAP14424 + (K100A) + MluI- | 5' TAGATACGCGTAGTCCTCTAGAATTTCTTTAAAGATGTCTT 3' (SEQ ID NO: 12) | 50 | 60 |
| HP-NAP$_{Y101H}$ | Hp26695-NAP14427 + (Y101H) + XhoI+ | 5' ACAAACATCTCGAGAAAGAATTTAAAGAGCTCTCTAACACC 3' (SEQ ID NO: 13) | 54 | 62 |
| | Hp26695-NAP14427 + (Y101H) + XhoI- | 5' TTCTTTCTCGAGATGTTTGTAGTCCTCTAGAATTTCTTTAAAGA 3' (SEQ ID NO: 14) | 54 | 62 |
| HP-NAP$_{E103A}$ | Hp26695-NAP14433 + (E103A) + ECORI+ | 5' TCTAGCAAAAGAATTCAAAGAGCTCTCTAACACCGCTGAAAA 3' (SEQ ID NO: 15) | 54 | 62 |
| | Hp26695-NAP14433 + (E103A) + ECORI- | 5' TCTTTGAATTCTTTTGCTAGATATTTGTAGTCCTCTAGAATTTCT 3' (SEQ ID NO: 16) | 54 | 62 |

TABLE 1-continued

Primers used in single site-directed mutagenesis

| HP-NAP mutants | primers | sequence | $T_{m\ pp}$ (° C.)[a] | $T_{m\ no}$ (° C.)[b] |
|---|---|---|---|---|
| HP-NAP$_{K104A}$ | Hp26695-NAP14436 + (K104A) + ECORI+ | 5' AAATATCTAGAAGCAGAATTCAAAGAGCTCTCTAACACCG 3' (SEQ ID NO: 17) | 50 | 56 |
| | Hp26695-NAP14436 + (K104A) + ECORI- | 5' AATTCTGCTTCTAGATATTTGTAGTCCTCTAGAATTTCTTT 3' (SEQ ID NO: 18) | 50 | 56 |

[a]$T_{m\ pp}$ (° C.) was calculated based on the overlapping region of primers.
[b]$T_{m\ no}$ (° C.) was calculated based on the matched region between primers and the DNA template.

Expression of Recombinant HP-NAP and Recombinant MBP-HP-NAP$_{R77-E116}$ in E. coli BL21 (DE3)

E. coli BL21 (DE3) harboring pET42a-NAP expression plasmid, the plasmids expressing HP-NAP with the desired point mutations, or pMAL c2g HP-NAP$_{R77-E116}$ were streaked on a LB agar plate containing 50 µg/ml kanamycin and incubated at 37° C. for 16 hours. A single colony of each above mentioned E. coli was picked and inoculated into 5 ml of LB containing 50 µg/ml kanamycin and shaken at 170 rpm at 37° C. for 16 hours. The volume of 0.1 ml of the overnight culture was then inoculated into 10 ml LB containing 50 µg/ml kanamycin and shaken at 170 rpm at 37° C. for 2 hours. To induce the expression of HP-NAP, HP-NAP mutants, and MBP-HP-NAP$_{R77-E116}$, 4 µl of 1 M isopropyl β-D-1-thiogalactopyranoside (IPTG) was added to the culture to a final concentration of 0.4 mM and then shaking at 170 rpm at 37° C. for 3 hours. Subsequently, the cells were centrifuged at 6,000×g at 4° C. for 15 minutes to remove the supernatant and stored at −70° C.

Bacterial Cell Lysis

The cell pellet from 3 ml of E. coli culture expressing recombinant HP-NAP or HP-NAP mutants were re-suspended in 1 ml of 20 mM Tris-HCl and 50 mM NaCl buffer (pH 9.0) containing 0.13 µM PMSF, 0.03 µM N-alpha-tosyl-L-lysinyl-chloromethylketone (TLCK) and 0.03 µM N-tosyl-L-phenylalaninyl-chloromethylketone (TPCK). The cell pellet from 20 ml of H. pylori culture were re-suspended in 1 ml of Dulbecco's phosphate-buffered saline (D-PBS) buffer containing 0.13 µM PMSF, 0.03 µM TLCK, and 0.03 µM TPCK. The bacterial suspensions were disrupted by an ultrasonic processor SONICS VCX-750 at 4° C. with 25% amplitude, with independent ON and OFF pulse cycles of 5 seconds and 10 seconds, respectively, and processing time of 4.5 minutes.

Purification of HP-NAP and HP-NAP Mutants

The E. coli lysates containing HP-NAP or HP-NAP mutants were centrifuged at 30,000×g at 4° C. for 1 hour to separate insoluble and soluble proteins by using Hitachi himac CS150NX table top micro-centrifuge with S80AT3 rotor (Hitachi Koki Co. Ltd., Tokyo, Japan). The supernatant was collected as the soluble protein fraction. These soluble protein fractions with different concentrations were first adjusted from pH 9.0 to pH 8.0 by the addition of 1 N HCl and then diluted with 20 mM Tris-HCl and 50 mM NaCl buffer (pH 8.0) to a protein concentration of 0.5 mg/ml. A volume of 600 µl of these soluble proteins (0.5 mg/ml) was then mixed with 200 µl of DEAE Sephadex resin at a volume ratio of 3:1. The slurries were then placed into an Eppendorf tube and left shaken on a rotator at 4° C. for 30 minutes. The slurries were centrifuged at 10,000×g at 4° C. for 30 seconds to obtain a supernatant which was retained as the unbound fraction. The unbound fractions containing purified recombinant HP-NAP or HP-NAP mutants were subjected to sodium dodecyl sulfate polyacrylamide gel electrophoresis (SDS-PAGE) on 15% gels and western-blot analysis. Recombinant HP-NAP used for stimulating neutrophils was purified by two consecutive gel filtration steps using a XK 16/100 column packed with Sephacryl S-300 high resolution resin (Sephacryl S-300 HR) (GE Healthcare Bio-Sciences) and a HiLoad 16/60 Superdex 200 prep grade (Superdex 200 pg) gel filtration column (GE Healthcare Bio-Sciences) as previously described (Wang et al., 2008).

Production of Recombinant MBP-HP-NAP$_{R77-E116}$

The cell pellet from 200 ml of E. coli culture expressing recombinant MBP-HP-NAP$_{R77-E116}$ were re-suspended in 20 ml of 20 mM Tris-HCl, pH 7.4, 200 mM NaCl, 1 mM EDTA and 1 mM dithiothreitol (DTT) containing 0.13 µM PMSF, 0.03 µM TLCK, and 0.03 µM TPCK. The bacterial suspensions were disrupted by seven passes through an Emulsiflex C3 high-pressure homogenizer (Avestin) at a range of 15,000-20,000 psi. The lysates were centrifuged at 30,000×g at 4° C. for 1 hour to separate insoluble and soluble proteins by using a Hitachi himac CP80WX ultracentrifuge (Hitachi Koki Co. Ltd., Tokyo, Japan). The supernatant was collected as the soluble protein fraction.

The MBPTrap 1 ml column (GE Healthcare Bio-Sciences) were pre-equilibrated with 20 mM Tris-HCl, pH 7.4, 200 mM NaCl, 1 mM EDTA, and 1 mM DTT, at a flow rate of 0.5 ml/min by ÄKTA Purifier (GE Healthcare). A volume of 20 ml of the soluble proteins containing recombinant MBP-HP-NAP$_{R77-E116}$ in 20 mM Tris-HCl, pH 7.4, 200 mM NaCl, 1 mM EDTA, and 1 mM DTT were loaded onto a MBPTrap 1 ml column. The column was then eluted with 20 mM Tris-HCl, pH 7.4, 200 mM NaCl, 1 mM EDTA, 1 mM DTT and 10 mM maltose, at a flow rate of 1 ml/min by ÄKTA Purifier. The elution fractions containing recombinant MBP-HP-NAP$_{R77-E116}$ were collected.

Western-Blot Analysis

The whole cell lysates of recombinant HP-NAP and HP-NAP mutants were analyzed by SDS-PAGE on a 15% gel and then transferred to a polyvinylidene difluoride (PVDF) membrane or a nitrocellulose (NC) membrane at 100V for 1 hour at 4° C. The membrane was incubated in Ponceau S staining solution (0.1% (w/v) Ponceau S in 1% (v/v) acetic acid) with shaking at room temperature for 5 minutes and briefly washed by deionized water. The image of the stained membrane was acquired using a LAS-3000 imaging system (Fujifilm, Tokyo, Japan) and quantification was performed using Multi Gauge Ver3.0 image analysis software (Fujifilm). The membrane was then incubated in Tris-buffered saline with 0.1% Tween-20 (TBS-T) containing 5% non-fat milk to block the non-specific binding at room temperature with shaking for 1 hour and probed with the primary antibody at 4° C. with shaking for 16 hours. After being washed three times with TBS-T for 10 minutes each time, the membrane was probed with horseradish peroxidase (HRP)-conjugated mouse secondary antibody at a dilution factor of 1:5000 in TBS-T containing 5% non-fat milk at room temperature with shaking for 1 hour. The enhanced chemiluminescence assay (ECL) western blotting detection reagents was used to visualized the signal, which was detected by LAS-3000 imaging system (Fujifilm, Tokyo, Japan).

Recombinant HP-NAP-Based ELISA

Ninety-six-well ELISA plates (Nunc) were coated with 0.3 µg recombinant HP-NAP or HP-NAP mutants in 100 µl bicarbonate buffer, pH 9.0, for each well at room temperature for 16 hours. Each well was washed with 300 µl phosphate buffered saline, pH 7.4, with 0.1% tween-20 (PBS-T) buffer three times for 10 minutes each time and then blocked with 250 µl PBS buffer with 1% bovine serum albumin (BSA) for 2 hours. After another three washes with PBS-T buffer, the antibodies with various concentrations in 100 µl PBS-T buffer with 1% BSA were added into each well and the plate was incubated at room temperature for 1 hour. Then, the horseradish peroxidase (HRP)-conjugated secondary antibody was loaded into each well and the plate was incubated at room temperature for 1 hour. The color was developed using 3,3',5,5'-tetramethylbenzidine (TMB) peroxidase substrate. The reaction was terminated by the addition of 2 N $H_2SO_4$, and the absorbance at 450 nm was measured by Bio-rad iMark microplate absorbance reader (Bio-rad).

Isolation of Human Neutrophils

Peripheral blood was collected in a test tube with sodium heparin by venipuncture from a healthy adult volunteer, who signed informed consents under the approval of the Institutional Review Board (IRB) of Mackay Memorial Hospital, Taipei, Taiwan. Heparinized blood with a volume of 9 ml was mixed with an equal volume of 3% dextran 500 in 0.9% saline solution. After dextran sedimentation of erythrocytes at room temperature for 20 minutes and centrifugation of leukocyte-rich plasma at 250×g at 4° C. for 10 minutes, the pellet was re-suspended with 9 ml ice-cold 0.9% saline solution. The leukocyte suspension was layered onto 9 ml Ficoll-Paque PLUS (GE Healthcare Bio-Sciences) and then centrifuged at 400×g at 20° C. for 40 minutes with no brake. The pellet rich in granulocytes, including neutrophils, was re-suspended in 20 ml ice-cold 0.2% saline solution for exactly 30 seconds followed by the addition of 20 ml ice-cold 1.6% saline solution for erythrocytes lysis. The mixture was centrifuged at 250×g at 4° C. for 6 minutes. This step of hypotonic lysis was repeated two to three times until a clean pellet was obtained. The final cell pellet was re-suspended in the 1 ml of D-PBS, pH 7.2, containing 5 mM glucose (D-PBS-G) and kept at 4° C. until use within 5 hours. The viability of neutrophils was assessed by trypan blue exclusion test on hemacytometer. The cell suspension containing $1\times10^5$ cells was placed on a slide, and then centrifuged at 72×g (600 rpm) at room temperature for 6 minutes by using Cytospin centrifuge. After centrifugation, the slides were allowed to air-dry and stained with Liu stain A for 30 seconds. Then, the slides were stained with Liu stain B for 90 seconds and rinsed with double distilled water. The appearance of the stained cells was observed by using Zeiss Axiovert 200 with 400× magnification (Carl Zeiss, Jena, Germany) The purity of neutrophils was determined by counting at least 700 cells in each preparation. Neutrophils were obtained with viability exceeding 98.1% and purity exceeding 96.3% in each preparation.

Measurement of Reactive Oxygen Species

Antibody X at a concentration of 13.5 µg/ml was used for pre-incubation with 1.4 µM HP-NAP at room temperature for 1 hour. The human neutrophils with a cell number of $1\times10^5$ cells were suspended in 50 µl of D-PBS, pH 7.2, containing 5 mM glucose (D-PBS-G) and then added into a black 96-well plate (Nunc) pre-incubated at 37° C. Subsequently, 150 µl of mixture containing 0.9 mM $CaCl_2$, 0.5 mM $MgCl_2$, 13.4 µM $H_2$DCF-DA and individual stimulus in D-PBS, pH 7.2, was added into each well to a final reaction volume of 200 µl. The final concentrations of $H_2$DCFDA and recombinant HP-NAP were 10 µM and 1 µM, respectively. The final concentration of antibody X was 10 µg/ml. The fluorescence was measured at 37° C. from 0 to 240 min with a 30 min interval. The emission of fluorescence was monitored in triplicate with a Wallac 1420-012 VICTOR 3 multilabel counter (Perkin-Elmer, MA, USA) by using an excitation wavelength of 485 nm and an emission wavelength of 538 nm.

Example 1

Detection of *Helicobacter pylori* Neutrophil-Activating Protein (HP-NAP) by the Antibody X The present invention uses a commercial IgG/M2 monoclonal antibody (Sigma, F-3165), designated as antibody X, in the following experiments. Another commercial IgG/M1 monoclonal antibody (Sigma, F-3040), designated as antibody Y, is used as a control. These antibodies, X and Y, can detect their original target proteins with the amino acid sequence DYKDDDDK (SEQ ID NO:1), also named a FLAG-tag. However, this sequence is not present in *Helicobacter pylori* neutrophil-activating protein (HP-NAP). To determine whether HP-NAP could be detected by the antibody X, recombinant HP-NAP of *H. pylori* 26695, whole cell lysates of HEK293 cells overexpressing an original target protein of the antibody X as a positive control, and whole cell lysates of HEK293 cells were subjected to western-blot analysis by using the antibody X. The antibody Y, which could detect the original target protein of antibody X, was also used in western-blot analysis. As shown in FIG. 1, the recombinant HP-NAP was detected by antibody X as a protein band of 17 kDa using western-blot analysis. Both antibodies X and Y detected their target protein overexpressed in the HEK 293 cells and some non-specific proteins expressed in HEK 293 cells. However, the antibody Y could not detect recombinant HP-NAP by western-blot analysis. The black arrowhead shown in FIG. 1 indicates the target protein of antibodies X and Y; the white arrowhead indicates non-specific proteins detected by antibodies X and Y; the striped arrowhead indicates HP-NAP. These results indicated that antibody X could detect the denatured recombinant HP-NAP of *H. pylori* 26695 in addition to its original target protein.

Figure 2:
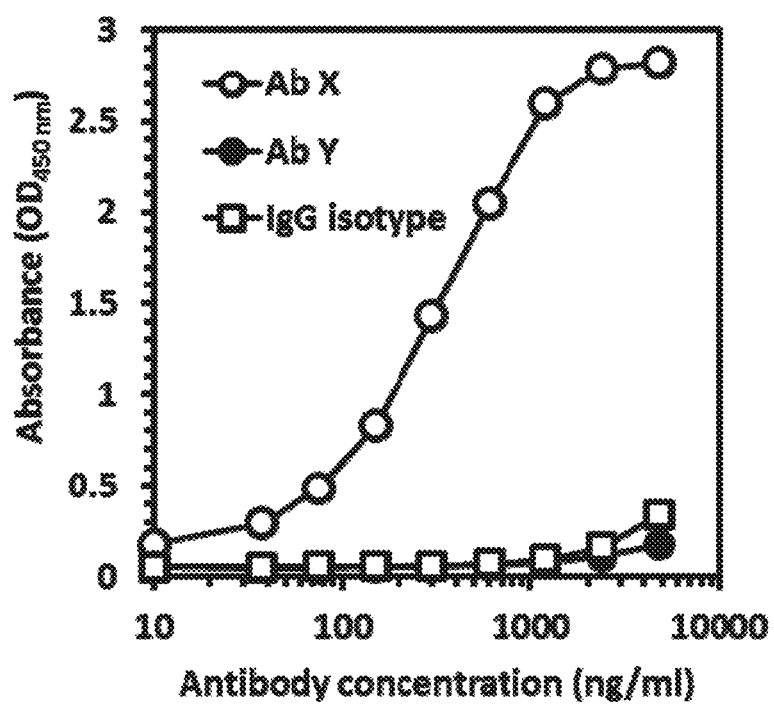
FIG. 2 shows detection of recombinant HP-NAP in its native form by recombinant HP-NAP-based enzyme linked immunosorbent assay (ELISA) using antibody X.

Next, whether the recombinant HP-NAP of *H. pylori* 26695 could be detected by antibody X was examined using ELISA. As shown in FIG. 2, the antibody X could detect recombinant HP-NAP at concentrations from 10 ng/ml to 4,800 ng/ml. While the recombinant HP-NAP could be detected with a reasonable signal by antibody X at the concentration of 600 ng/ml, there is no detectable signal for using the antibodies Y and IgG isotype control at that concentration. This result indicated that the antibody X can recognize the native form of HP-NAP. Taken together, the antibody X can detect recombinant HP-NAP of *H. pylori* 26695 by using both western-blot and recombinant HP-NAP-based ELISA through the recognition of the denatured and native forms of this protein, respectively.

Figure 3:
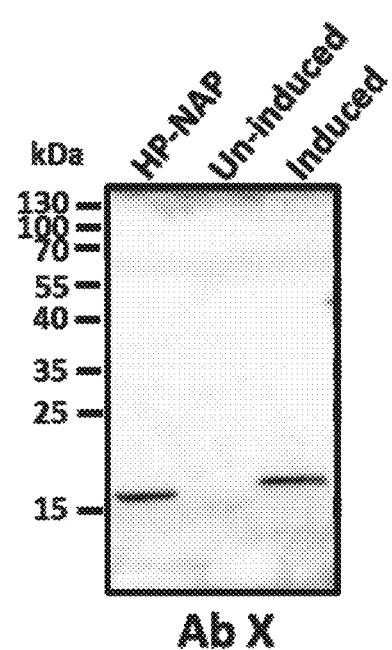
FIG. 3 shows detection of recombinant HP-NAP expressed in *E. coli* BL21 (DE3) by western-blot analysis using antibody X.

To further verify whether the antibody X could specifically detect the recombinant HP-NAP of *H. pylori* 26695 expressed in *Escherichia coli* (*E. coli*) without further purification, the whole cell lysates of *E. coli* BL21 (DE3) expressing the recombinant HP-NAP was subjected to western-blot analysis. The whole cell lysates which contained 4 µg of proteins from un-induced and IPTG-induced *E. coli* BL21 (DE3) harboring the vector expressing recombinant HP-NAP and 1 µg of purified recombinant HP-NAP were subjected to SDS-PAGE and then analyzed by western-blot. As shown in FIG. 3, only one protein band of 17 kDa was detected by the antibody X. These results indicate that the antibody X is able to specifically detect recombinant HP-NAP but not the endogenous proteins expressed by *E. coli*.

Example 2

Analysis of the Epitope of the Antibody X on HP-NAP

Figure 4:
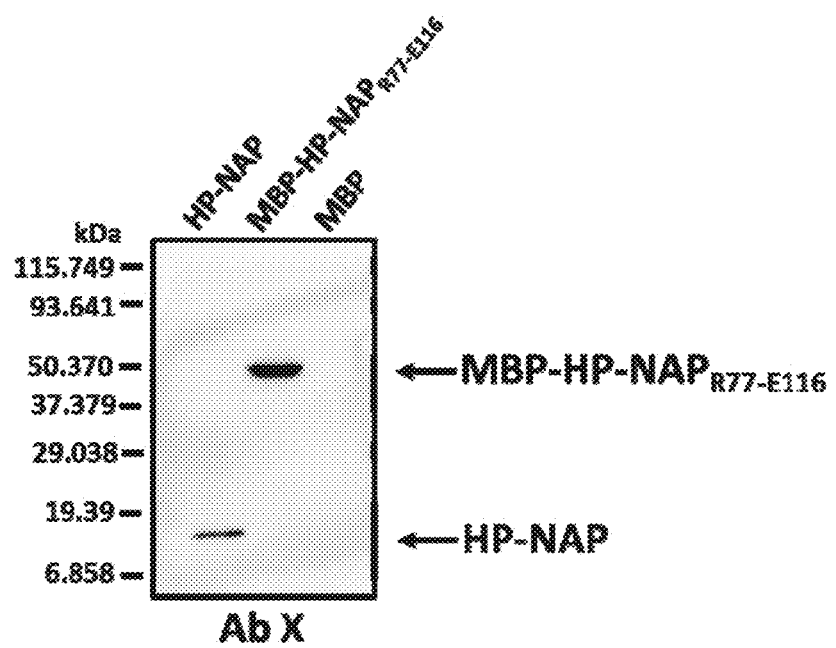
FIG. 4 shows detection of HP-NAP and recombinant maltose-binding protein (MBP)-tagged protein containing residues Arg77 to Glu116 of HP-NAP (MBP-tagged HP-NAP$_{R77-E116}$) by western-blot analysis using antibody X.

To determine the location of epitope of the antibody X on HP-NAP, purified recombinant maltose-binding protein (MBP)-tagged protein containing residues Arg77 to Glu116 of HP-NAP (MBP-HP-NAP$_{R77-E116}$), HP-NAP and MBP protein were subjected to western-blot analysis with antibody X. As shown in FIG. 4, the antibody X could detect recombinant HP-NAP (a protein band of 17 kDa) and MBP-HP-NAP$_{R77-E116}$ (a protein band of 47 kDa) but not MBP protein. These results indicate that the amino acid residues ranging from Arg77 to Glu116 of HP-NAP can be detected by antibody X.

The antibody X recognizes the DYKDDDDK (SEQ ID NO:1) peptide. However, there is no such amino acid sequence except the first three amino acids, DYK, present in HP-NAP. They are amino acid residues Asp98, Tyr99, and Lys100 of HP-NAP. To determine whether these three amino acid residues are required for the detection of HP-NAP by antibody X, Asp98, Tyr99, and Lys100 were mutated to Ala. Also, Glu103 and Lys104 were chosen for site-direct mutagenesis. For example, a mutation of the residue Asp98 of HP-NAP to Ala is represented as HP-NAP$_{D98A}$. Then, the whole cell lysates of *E. coli* expressing the above mentioned HP-NAP mutants, HP-NAP$_{D98A}$, HP-NAP$_{Y99A}$, HP-NAP$_{K100A}$, HP-NAP$_{E103A}$, and HP-NAP$_{K104A}$, were subjected to western-blot analysis with antibody X. The amounts of the recombinant HP-NAP and its mutants in the whole cell lysates were quantified by ponceau S staining of the blotting membrane. The signal intensity of the HP-NAP mutants in western-blot was normalized to that of the wild-type HP-NAP.

Figure 5:
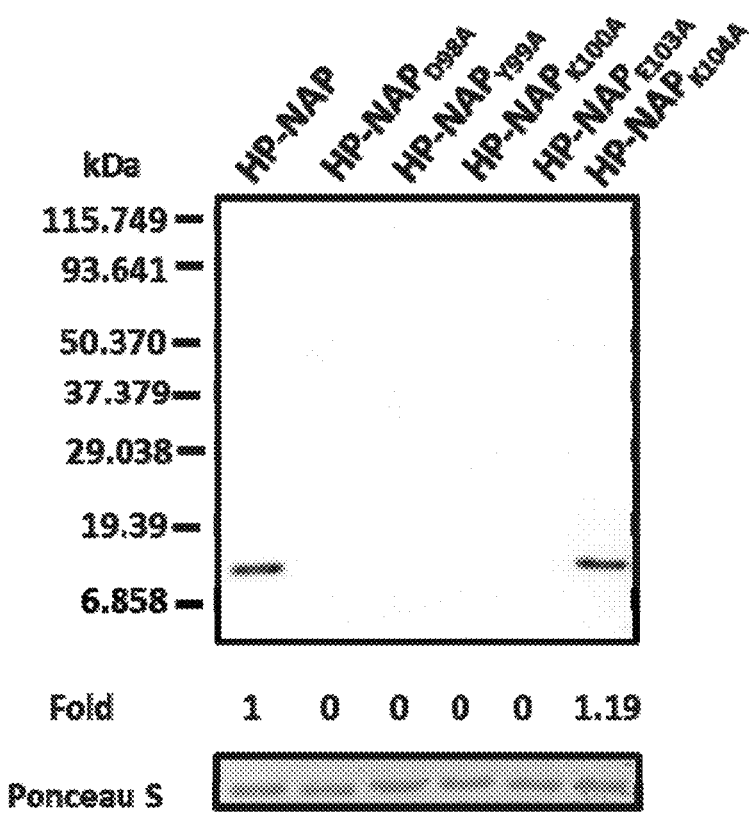
FIG. 5 shows detection of recombinant HP-NAP mutants, HP-NAP$_{D98A}$, HP-NAP$_{Y99A}$, HP-NAP$_{K100A}$, HP-NAP$_{E103A}$, and HP-NAP$_{K104A}$, by western-blot analysis using antibody X; each mutant is prepared by single site-directed mutagenesis for analyzing the epitope of antibody X.

As shown in FIG. 5, among the mutants generated, the antibody X could not detect HP-NAP$_{D98A}$, HP-NAP$_{Y99A}$, HP-NAP$_{K100A}$, and HP-NAP$_{E103A}$ mutants by western-blot analysis. These results indicate that the four amino acid residues, Asp98, Tyr99, Lys100, and Glu103, of HP-NAP are required for the detection of HP-NAP by the antibody X. In other words, $D_{98}Y_{99}K_{100}XXE_{103}$ (SEQ ID NO:2) is the epitope sequence on HP-NAP and is recognized by the antibody X. Although a control antibody Y could detect the amino acid sequence of DYKDDDDK (SEQ ID NO:1), this recognition was limited to the DYKDDDDK sequence (SEQ ID NO:1) located at the N-terminus of a protein. On the other hand, the antibody X of the present invention could recognize the amino acid sequence of SEQ ID NO:2 at any position of a protein.

Figure 6:
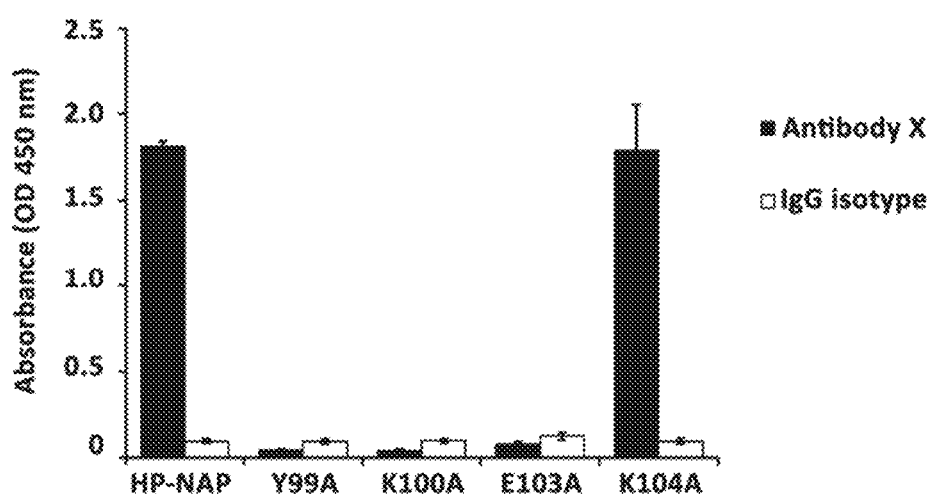
FIG. 6 shows detection of recombinant HP-NAP mutants, HP-NAP$_{Y99A}$, HP-NAP$_{K100A}$, HP-NAP$_{E103A}$, and HP-NAP$_{K104A}$, by recombinant HP-NAP-based ELISA using antibody X.

To determine if these residues are also required for the detection of HP-NAP by antibody X in recombinant HP-NAP-based ELISA, the HP-NAP mutants, HP-NAP$_{D98A}$, HP-NAP$_{Y99A}$, HP-NAP$_{K100A}$, HP-NAP$_{E103A}$, and HP-NAP$_{K104A}$, were further purified and used as coating antigens in ELISA. Since HP-NAP$_{D98A}$ is present as an insoluble protein, only the other four HP-NAP mutants were used as coating antigens in recombinant HP-NAP-based ELISA. As shown in FIG. 6, the antibody X at the concentration of 600 ng/ml could not detect HP-NAP$_{Y99A}$, HP-NAP$_{K100A}$, and HP-NAP$_{E103A}$ mutants. Thus, the amino acid residues, Tyr99, Lys100, and Glu103, of HP-NAP are also required for the detection of native form of HP-NAP by the antibody X.

Example 3

Detection of HP-NAP of *H. pylori* Strains, 26695, NCTC 11639, and NCTC 11637

As shown in FIG. 7, HP-NAP is highly conserved among the twelve *H. pylori* strains based on amino acid sequence alignment by ClustalW. The non-conserved amino acid residues of HP-NAP among these twelve strains are highlighted in gray. Below the protein sequence, an asterisk, a colon and a period are used to indicate the conserved residues, the conservative mutations and the semi-conservative mutations. The residues from Arg77 to Glu116 of HP-NAP are underlined.

Figure 8:
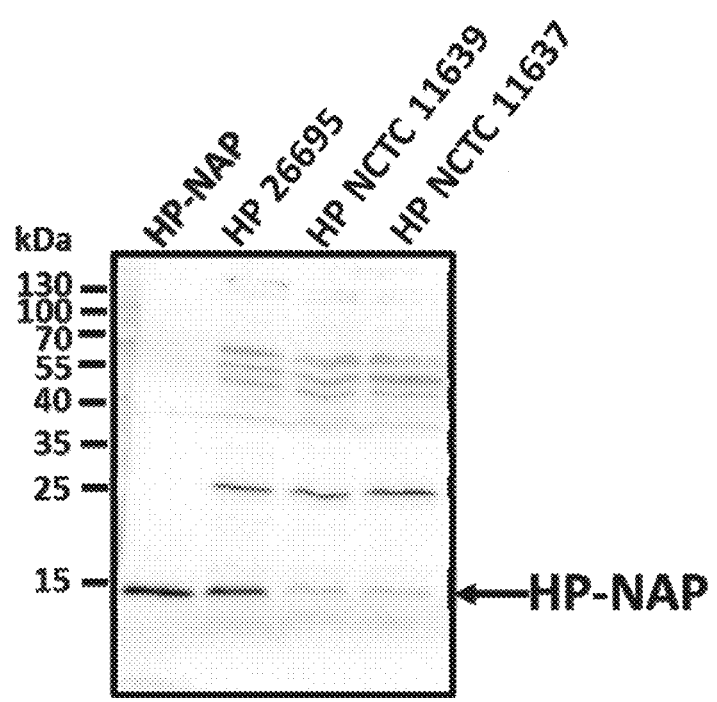
FIG. 8 shows detection of endogenous HP-NAP from three *H. pylori* strains, 26695, NCTC 11639, and NCTC 11637, by western-blot analysis using antibody X.

As shown in FIG. 7, there are nine non-identical residues among the 114 amino acid residues of HP-NAP, whereas only three non-identical residues are found for the residues ranging from Arg77 to Glu116 of HP-NAP. To determine whether the antibody X could detect endogenous HP-NAP from different *H. pylori* strains, 1 µg of purified recombinant HP-NAP and the whole cell lysates which contained 48 µg of proteins from *H. pylori* 26695, NCTC 11639, and NCTC 11637 strains were subjected to SDS-PAGE and analyzed by western-blot. As shown in FIG. 8, the antibody X could detect endogenous HP-NAP from the whole cell lysate of *H. pylori* 26695 strain with similar intensity to recombinant HP-NAP. However, the signal intensities of the endogenous HP-NAP from whole cell lysates of *H. pylori* NCTC 11639 and NCTC 11637 were much lower than that of *H. pylori* 26695 strain. Taken together, the antibody X could detect the endogenous HP-NAP of *H. pylori* strains 26695, NCTC 11639, and NCTC 11637.

The reason why the antibody X detects HP-NAP from all three *H. pylori* strains with different intensity might be due to the differences in the amino acid sequences of HP-NAP from these three *H. pylori* strains. As shown in FIG. 7, amino acid sequence alignment of HP-NAP between *H. pylori* strain 26695 and eleven other *H. pylori* strains shows that there are only two non-identical amino acid residues close to the epitope of antibody X on HP-NAP of *H. pylori* 26695. These two amino acid residues are Glu97 and Tyr101. We then generated two HP-NAP mutants named HP-NAP$_{Y101H}$ and HP-NAP$_{E97GY101H}$, which mimic HP-NAP of *H. pylori* strains NCTC 11639 and NCTC 11637 respectively (Table 2), to study the effect of such mutations on HP-NAP detection by antibody X.

TABLE 2

The list of the non-identical residues located at the amino acids residues ranging from Arg77 to Glu116 of HP-NAP of *H. pylori* strains, 26695, NTCT 11639, and NCTC 11637.

| *H. pylori* strains | Non-conserved residues | | HP-NAP mutants |
|---|---|---|---|
| | Residue 97 | Residue 101 | |
| 26695 | E | Y | — |
| NCTC 11639 | E | H | HP-NAP$_{Y101H}$ |
| NCTC 11637 | G | H | HP-NAP$_{E97GY101H}$ |

The whole cell lysates of E. coli expressing the wild-type HP-NAP, the HP-NAP$_{Y101H}$ mutant, and the HP-NAP$_{E97GY101H}$ mutant, were subjected to western-blot analysis with antibody X. The amounts of the recombinant HP-NAP and its mutants in the whole cell lysates were quantified by ponceau S staining of the blotting membrane. The signal intensity of the protein band for each HP-NAP mutant detected by western-blot analysis was normalized to that for the wild-type HP-NAP.

Figure 9:
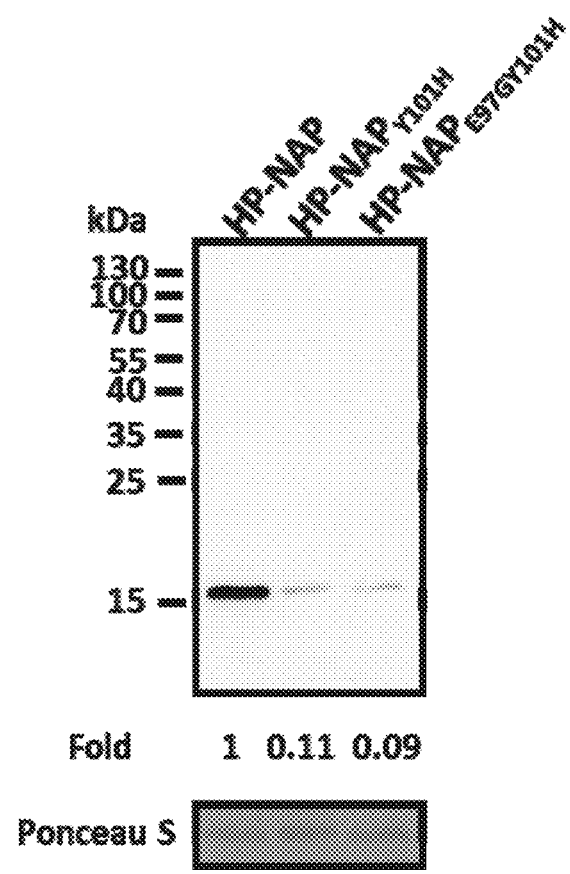
FIG. 9 shows detection of recombinant HP-NAP mutants, HP-NAP$_{Y101H}$, and HP-NAP$_{E97GY101H}$, by western-blot analysis using antibody X; each mutant is prepared by site-directed mutagenesis.

By western-blot analysis, the HP-NAP$_{Y101H}$ and HP-NAP$_{E97GY101H}$ mutants expressed in E. coli BL21 (DE3) were detected by the antibody X and their intensities were 11% and 9% compared to that of the wild-type HP-NAP, as shown in FIG. 9. The results indicate that the different sensitivities of antibody X in detecting HP-NAP of different H. pylori strains comes from the variation in the amino acid sequences of HP-NAP.

Furthermore, the purified wild-type HP-NAP, HP-NAP$_{Y101H}$ mutant, and HP-NAP$_{E97GY101H}$ mutant were subjected to recombinant HP-NAP-based ELISA analysis. The concentrations of the antibody X used in this analysis ranged from 10 ng/ml to 600 ng/ml.

Figure 10:
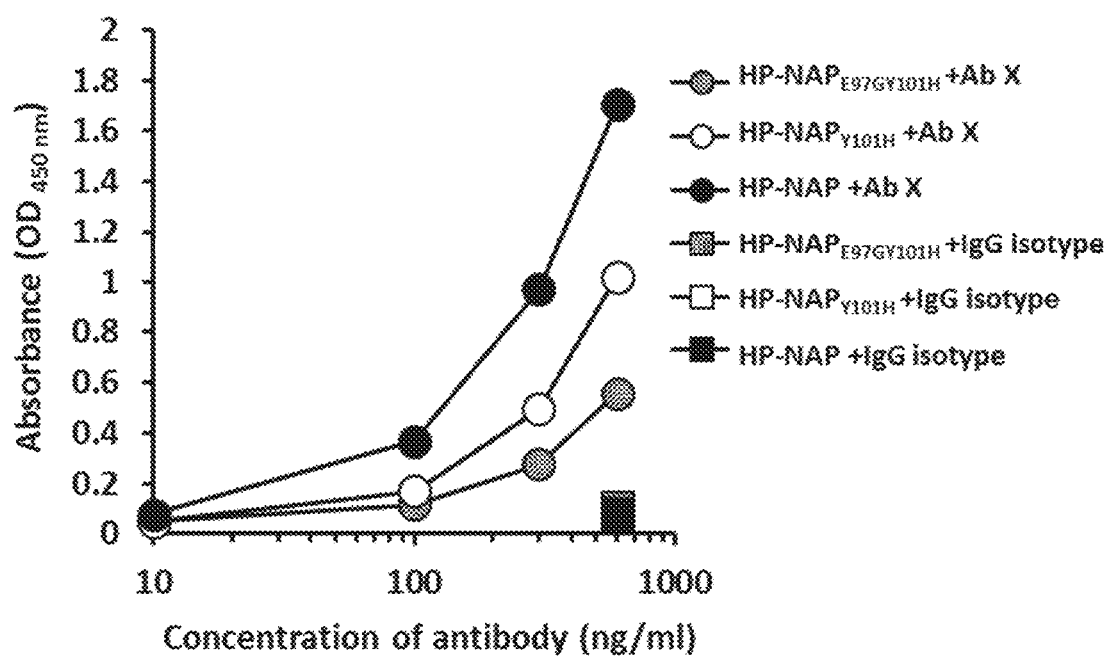
FIG. 10 shows detection of recombinant HP-NAP mutants, HP-NAP$_{E97GY101H}$, and HP-NAP$_{Y101H}$, by recombinant HP-NAP-based ELISA using antibody X.

By recombinant HP-NAP-based ELISA analysis, the antibody X at the concentration of 600 ng/ml was able to detect the HP-NAP$_{Y101H}$ and HP-NAP$_{E97GY101H}$ mutants and their signals were 60% and 33% compared to that of the wild-type HP-NAP, as shown in FIG. 10. The results indicate that the antibody X can detect the native forms of the HP-NAP$_{Y101H}$ and HP-NAP$_{E97GY101H}$ mutants with better sensitivities than their denatured forms. Thus, the antibody X can be used to detect endogenous HP-NAP from H. pylori strains.

Example 4

Figure 11A:
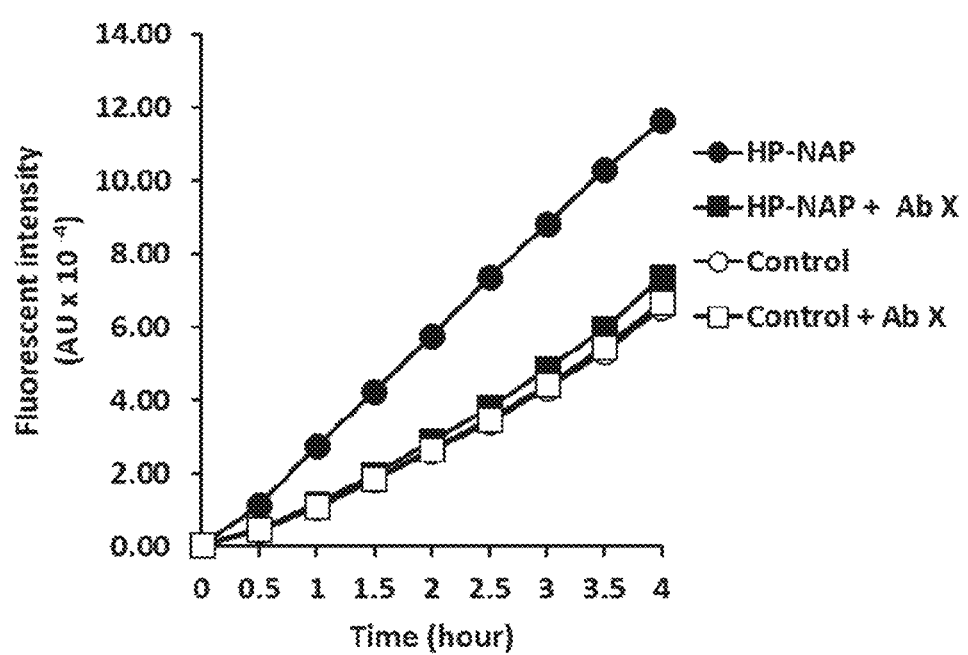
FIG. 11A shows the time-course of H$_2$DCF-DA fluorescence assay for analyzing the inhibitory effect of antibody X on HP-NAP-induced production of reactive oxygen species (ROS) by human neutrophils.
Figure 11B:
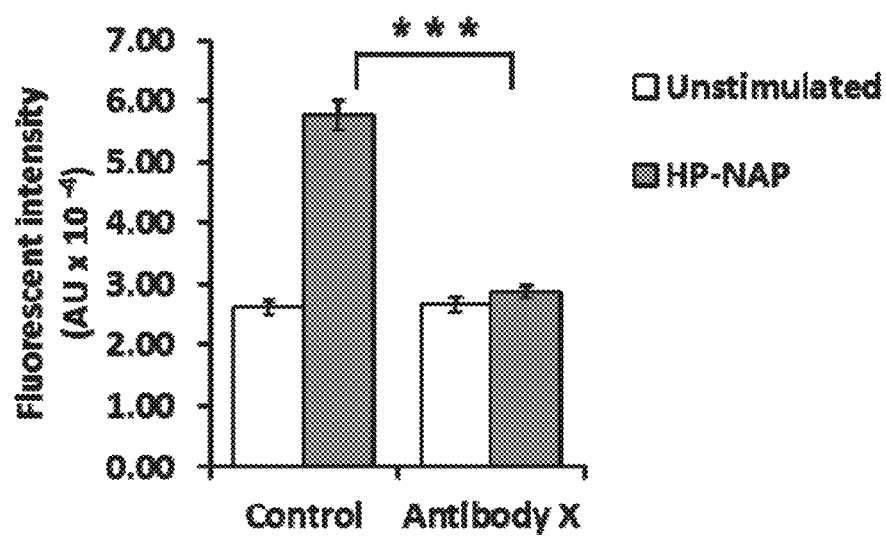
FIG. 11B shows the fluorescence intensity of neutrophils in H$_2$DCF-DA fluorescence assay for analyzing the inhibitory effect of antibody X on HP-NAP-induced ROS production by human neutrophils; asterisk indicates statistically significant difference (***, $p<0.001$).

Inhibition of HP-NAP-Induced Production of Reactive Oxygen Species (ROS) from Human Neutrophils by the Antibody X HP-NAP is able to trigger ROS production by human neutrophils (Evans et al., 1995; Satin et al., 2000). To determine whether antibody X can inhibit HP-NAP-induced ROS production by neutrophils, H$_2$DCF-DA-derived fluorescence assay was applied to measure the intracellular ROS level. As shown in FIG. 11A, the antibody X at the concentration of 10 μg/ml almost completely inhibit HP-NAP-induced ROS production by neutrophils. As shown in FIG. 11B, upon two hours of HP-NAP stimulation, the production of ROS was significantly inhibited by 93.2% in cells stimulated with HP-NAP pre-incubated with antibody X as compared to the HP-NAP-stimulated cells. These results indicate that the antibody X can serve as a blocking antibody of HP-NAP to inhibit its activity. Furthermore, HP-NAP can combine with anti-inflammatory agents, including but not limited to glucocorticoids, corticosteroids, T-cell blockers, purine analogs, pyrimidine analogs, alkylating agents, antifolates, antibiotics, and antibodies, for treating H. pylori infection.

The antibody X of the present invention inhibits HP-NAP-induced ROS production by neutrophils and serves as a blocking antibody of HP-NAP. It has been reported that HP-NAP binds to neutrophils via the structure of its C-terminus, especially the third and the forth helices which contains residues L69-L75 and S88-A113, and activates neutrophils. As mentioned, the antibody X can detect HP-NAP by recognizing the residues, D98, Y99, K100, and E103, on HP-NAP. Thus, the active site of HP-NAP should be located at the binding region for the antibody X at the forth helix of HP-NAP. In addition, it is considered that HP-NAP activates neutrophils to produce ROS through a PTX-sensitive GPCR. Thus, the antibody X of the present invention is able to block the binding of HP-NAP to the GPCR, and so inhibits HP-NAP-induced activation of neutrophil. Therefore, the antibody X of the present invention can inhibit the inflammatory responses initiated by immune cells that bear HP-NAP receptors.

According to the above mentioned examples, the antibody X can detect HP-NAP$_{Y101H}$ and HP-NAP$_{E97GY101H}$ mutants in their native forms with a one-third or two-third lower sensitivity compared to the wild-type HP-NAP. On the other hand, the antibody X shows a much lower sensitivity to these two HP-NAP mutants in their denatured forms. This result indicates that the antibody X performs better in detecting native HP-NAP from different H. pylori strains. Due to the advantage of this HP-NAP-based detection of various H. pylori strains by the antibody X, it is applicable to use the antibody X in indirect immunofluorescence testing (IIFT) to detect the presence of H. pylori in serum or other test samples. The antibody X can also be used in immunohistochemistry (IHC) or other immunoassays for detecting H. pylori.

In conclusion, the antibody X of the present invention can detect HP-NAP, and it can bind to the amino acid residues Arg77 to Glu116 of HP-NAP. Specifically, the antibody X recognizes the epitope of D$_{98}$Y$_{99}$K$_{100}$XXE$_{103}$ (SEQ ID NO:2) on HP-NAP, and thus it can be used to detects HP-NAP from various H. pylori strains. Furthermore, the antibody X can inhibit HP-NAP-induced ROS production by neutrophils and serve as a blocking antibody to HP-NAP. Therefore, the antibody X can be applied in diagnosing H. pylori infection and treating the infection via inhibiting the inflammatory responses ignited by H. pylori.

The present invention provides methods for diagnosing and treating *Helicobacter pylori* infection in a subject by using an ANTI-FLAG antibody and therefore shows obvious commercial values. Although the present invention has been described with reference to the preferred embodiments, it will be apparent to those skilled in the art that a variety of modifications and changes in form and detail may be made without departing from the scope of the present invention defined by the appended claims.

REFERENCES

Evans D J Jr, Evans D G, Takemura T, Nakano H, Lampert H C, Graham D Y, Granger D N, and Kvietys P R. (1995) Characterization of a *Helicobacter pylori* neutrophil-activating protein. *Infect Immun.* 63, 2213-2220.

Satin B, Del Giudice G, Della Bianca V, Dusi S, Laudanna C, Tonello F, Kelleher D, Rappuoli R, Montecucco C, and Rossi F. (2000) The neutrophil-activating protein (HP-NAP) of *Helicobacter pylori* is a protective antigen and a major virulence factor. *J Exp Med.* 191, 1467-1476.

Wang C A, Liu Y C, Du S Y, Lin C W, Fu H W. (2008) *Helicobacter pylori* neutrophil-activating protein promotes myeloperoxidase release from human neutrophils. *Biochem Biophys Res Commun.* 377, 52-56.

What is claimed is:

1. A method for diagnosing *Helicobacter pylori* infection in a subject, comprising the steps of:
   (a) providing a test sample from the subject;
   (b) contacting the test sample with an antibody that specifically recognizes SEQ ID NO: 1; and
   (c) detecting a binding of the antibody of step (b) to *Helicobacter pylori* neutrophil-activating protein (HP-NAP) produced by *H. pylori* in the test sample to determine the presence or absence of *H. pylori;*
   wherein *H. pylori* infection is diagnosed in the subject when the binding of the antibody of step (b) to the HP-NAP is detected.

2. The method of claim 1, wherein the antibody of step (b) binds to an epitope on the HP-NAP.

3. The method of claim 2, wherein the epitope comprises the amino acid sequence of SEQ ID NO:2.

4. The method of claim 1, wherein the HP-NAP is in a native form or a denatured form.

5. The method of claim 1, wherein the test sample is selected from the group consisting of gastric fluid, intestinal fluid, blood, serum, urine, feces and combinations thereof.

6. The method of claim 1, wherein step (c) is conducted using an assay selected from the group consisting of Western-blotting, enzyme-linked immunosorbent assay, indirect immunofluorescence testing (IIFT), immunohistochemical staining, immunoprecipitation and combinations thereof.

7. A method for treating *Helicobacter pylori* infection in a subject, comprising administrating to the subject an effective amount of an antibody that specifically recognizes SEQ ID NO: 1, wherein the antibody inhibits the activity of *Helicobacter pylori* neutrophil-activating protein (HP-NAP).

8. The method of claim 7, wherein the antibody further combines with an anti-inflammatory agent for treating *H. pylori* infection.

9. The method of claim 8, wherein the anti-inflammatory agent is selected from the group consisting of glucocorticoids, corticosteroids, T-cell blockers, purine analogs, pyrimidine analogs, alkylating agents, antifolates, antibiotics, antibodies and combinations thereof.

10. A method for recognition of *Helicobacter pylori* neutrophil-activating protein (HP-NAP), comprising contacting the HP-NAP with an antibody which specifically recognizes SEQ ID NO: 2.

11. A method for recognition and inhibition of *Helicobacter pylori* neutrophil-activating protein (HP-NAP), comprising contacting the HP-NAP with an antibody which specifically recognizes SEQ ID NO: 2 to inhibit the activity of the HP-NAP.

* * * * *

SEQUENCE LISTING

<160> NUMBER OF SEQ ID NOS: 30

<210> SEQ ID NO 1
<211> LENGTH: 8
<212> TYPE: PRT
<213> ORGANISM: Artificial sequence
<220> FEATURE:
<223> OTHER INFORMATION: FLAG tag

<400> SEQUENCE: 1

Asp Tyr Lys Asp Asp Asp Asp Lys
1               5

<210> SEQ ID NO 2
<211> LENGTH: 6
<212> TYPE: PRT
<213> ORGANISM: Artificial sequence
<220> FEATURE:
<223> OTHER INFORMATION: HP-NAP epitope
<220> FEATURE:
<221> NAME/KEY: misc_feature
<222> LOCATION: (4)..(5)
<223> OTHER INFORMATION: Xaa can be any naturally occurring amino acid

<400> SEQUENCE: 2

Asp Tyr Lys Xaa Xaa Glu
1               5

<210> SEQ ID NO 3
<211> LENGTH: 33
<212> TYPE: DNA
<213> ORGANISM: Artificial sequence
<220> FEATURE:
<223> OTHER INFORMATION: PCR primer

<400> SEQUENCE: 3
ataaggatcc cgtgttaaag aagaaactaa aac                                    33

<210> SEQ ID NO 4
<211> LENGTH: 36
<212> TYPE: DNA
<213> ORGANISM: Artificial sequence
<220> FEATURE:
<223> OTHER INFORMATION: PCR primer

<400> SEQUENCE: 4
ttaataagct ttaattcttt ttcagcggtg ttagag                                 36

<210> SEQ ID NO 5
<211> LENGTH: 42
<212> TYPE: DNA
<213> ORGANISM: Artificial sequence
<220> FEATURE:
<223> OTHER INFORMATION: Primer for single site-directed mutagenesis

<400> SEQUENCE: 5
acaaacatct cgagaaagaa tttaaagagc tctctaacac cg                          42

<210> SEQ ID NO 6
<211> LENGTH: 45
<212> TYPE: DNA
<213> ORGANISM: Artificial sequence
<220> FEATURE:
<223> OTHER INFORMATION: Primer for single site-directed mutagenesis

<400> SEQUENCE: 6
ttctttctcg agatgtttgt agtcccctag aatttcttta aagat                       45

<210> SEQ ID NO 7
<211> LENGTH: 45
<212> TYPE: DNA
<213> ORGANISM: Artificial sequence
<220> FEATURE:
<223> OTHER INFORMATION: Primer for single site-directed mutagenesis

<400> SEQUENCE: 7
aaattctcga ggcttacaaa tatctagaaa aagaatttaa agagc            45

<210> SEQ ID NO 8
<211> LENGTH: 43
<212> TYPE: DNA
<213> ORGANISM: Artificial sequence
<220> FEATURE:
<223> OTHER INFORMATION: Primer for single site-directed mutagenesis

<400> SEQUENCE: 8
tttgtaagcc tcgagaattt ctttaaagat gtctttagag tgg              43

<210> SEQ ID NO 9
<211> LENGTH: 43
<212> TYPE: DNA
<213> ORGANISM: Artificial sequence
<220> FEATURE:
<223> OTHER INFORMATION: Primer for single site-directed mutagenesis

<400> SEQUENCE: 9
attctcgagg acgccaaata tctagaaaaa gaatttaaag agc              43

<210> SEQ ID NO 10
<211> LENGTH: 43
<212> TYPE: DNA
<213> ORGANISM: Artificial sequence
<220> FEATURE:
<223> OTHER INFORMATION: Primer for single site-directed mutagenesis

<400> SEQUENCE: 10
tttggcgtcc tcgagaattt ctttaaagat gtctttagag tgg              43

<210> SEQ ID NO 11
<211> LENGTH: 40
<212> TYPE: DNA
<213> ORGANISM: Artificial sequence
<220> FEATURE:
<223> OTHER INFORMATION: Primer for single site-directed mutagenesis

<400> SEQUENCE: 11
aggactacgc gtatctagaa aaagaattta aagagctctc                  40

<210> SEQ ID NO 12
<211> LENGTH: 41
<212> TYPE: DNA
<213> ORGANISM: Artificial sequence
<220> FEATURE:
<223> OTHER INFORMATION: Primer for single site-directed mutagenesis

<400> SEQUENCE: 12
tagatacgcg tagtcctcta gaatttcttt aaagatgtct t                41

<210> SEQ ID NO 13
<211> LENGTH: 41
<212> TYPE: DNA
<213> ORGANISM: Artificial sequence
<220> FEATURE:

```
<223> OTHER INFORMATION: Primer for single site-directed mutagenesis

<400> SEQUENCE: 13
acaaacatct cgagaaagaa tttaaagagc tctctaacac c                41

<210> SEQ ID NO 14
<211> LENGTH: 44
<212> TYPE: DNA
<213> ORGANISM: Artificial sequence
<220> FEATURE:
<223> OTHER INFORMATION: Primer for single site-directed mutagenesis

<400> SEQUENCE: 14
ttctttctcg agatgtttgt agtcctctag aatttcttta aaga             44

<210> SEQ ID NO 15
<211> LENGTH: 42
<212> TYPE: DNA
<213> ORGANISM: Artificial sequence
<220> FEATURE:
<223> OTHER INFORMATION: Primer for single site-directed mutagenesis

<400> SEQUENCE: 15
tctagcaaaa gaattcaaag agctctctaa caccgctgaa aa               42

<210> SEQ ID NO 16
<211> LENGTH: 45
<212> TYPE: DNA
<213> ORGANISM: Artificial sequence
<220> FEATURE:
<223> OTHER INFORMATION: Primer for single site-directed mutagenesis

<400> SEQUENCE: 16
tctttgaatt cttttgctag atatttgtag tcctctagaa tttct            45

<210> SEQ ID NO 17
<211> LENGTH: 40
<212> TYPE: DNA
<213> ORGANISM: Artificial sequence
<220> FEATURE:
<223> OTHER INFORMATION: Primer for single site-directed mutagenesis

<400> SEQUENCE: 17
aaatatctag aagcagaatt caaagagctc tctaacaccg                  40

<210> SEQ ID NO 18
<211> LENGTH: 41
<212> TYPE: DNA
<213> ORGANISM: Artificial sequence
<220> FEATURE:
<223> OTHER INFORMATION: Primer for single site-directed mutagenesis

<400> SEQUENCE: 18
aattctgctt ctagatattt gtagtcctct agaatttctt t                41

<210> SEQ ID NO 19
<211> LENGTH: 144
<212> TYPE: PRT
<213> ORGANISM: Helicobacter pylori strain 26695

<400> SEQUENCE: 19

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
                20                  25                  30
```

```
Phe Phe Asn Val His Lys Ala Thr Glu Glu Ile Tyr Glu Glu Phe Ala
            35                  40                  45

Asp Met Phe Asp Asp Leu Ala Glu Arg Ile Val Gln Leu Gly His His
        50                  55                  60

Pro Leu Val Thr Leu Ser Glu Ala Ile Lys Leu Thr Arg Val Lys Glu
65                  70                  75                  80

Glu Thr Lys Thr Ser Phe His Ser Lys Asp Ile Phe Lys Glu Ile Leu
                85                  90                  95

Glu Asp Tyr Lys Tyr Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
    130                 135                 140
```

<210> SEQ ID NO 20
<211> LENGTH: 144
<212> TYPE: PRT
<213> ORGANISM: Helicobacter pylori strain NCTC11639

<400> SEQUENCE: 20

```
Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
            35                  40                  45

Asp Met Phe Asp Asp Leu Ala Glu Arg Ile Val Gln Leu Gly His His
        50                  55                  60

Pro Leu Val Thr Leu Ser Glu Ala Ile Lys Leu Thr Arg Val Lys Glu
65                  70                  75                  80

Glu Thr Lys Thr Ser Phe His Ser Lys Asp Ile Phe Lys Glu Ile Leu
                85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
    130                 135                 140
```

<210> SEQ ID NO 21
<211> LENGTH: 144
<212> TYPE: PRT
<213> ORGANISM: Helicobacter pylori strain NCTC11637

<400> SEQUENCE: 21

```
Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
            35                  40                  45

Asp Met Phe Asp Asp Leu Ala Glu Arg Ile Ala Gln Leu Gly His His
        50                  55                  60

Pro Leu Val Thr Leu Ser Glu Ala Leu Lys Leu Thr Arg Val Lys Glu
65                  70                  75                  80
```

Glu Thr Lys Thr Ser Phe His Ser Lys Asp Ile Phe Lys Glu Ile Leu
            85                  90                  95

Gly Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
            115                 120                 125

Leu Ala Lys Leu Gln Lys Ser Ile Trp Met Leu Glu Ala His Leu Ala
            130                 135                 140

<210> SEQ ID NO 22
<211> LENGTH: 144
<212> TYPE: PRT
<213> ORGANISM: Helicobacter pylori strain J99

<400> SEQUENCE: 22

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Gly Phe Ala
            35                  40                  45

Asp Met Phe Asp Asp Leu Ala Glu Arg Ile Val Gln Leu Gly His His
            50                  55                  60

Pro Leu Val Thr Leu Ser Glu Ala Ile Lys Leu Thr Arg Val Lys Glu
65                  70                  75                  80

Glu Thr Lys Thr Ser Phe His Ser Lys Asp Ile Phe Lys Glu Ile Leu
            85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
            115                 120                 125

Leu Ala Lys Leu Gln Lys Ser Ile Trp Met Leu Glu Ala His Leu Ala
            130                 135                 140

<210> SEQ ID NO 23
<211> LENGTH: 144
<212> TYPE: PRT
<213> ORGANISM: Helicobacter pylori strain OK310

<400> SEQUENCE: 23

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Gly Phe Ala
            35                  40                  45

Asp Met Phe Asp Asp Leu Ala Glu Arg Ile Val Gln Leu Gly His His
            50                  55                  60

Pro Leu Val Thr Leu Ser Glu Ala Leu Lys Leu Thr Arg Val Lys Glu
65                  70                  75                  80

Glu Thr Lys Thr Ser Phe His Ser Lys Asp Ile Phe Lys Glu Ile Leu
            85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
            115                 120                 125

```
Leu Ala Lys Leu Gln Lys Ser Ile Trp Met Leu Gln Ala His Leu Ala
        130                 135                 140
```

<210> SEQ ID NO 24
<211> LENGTH: 144
<212> TYPE: PRT
<213> ORGANISM: Helicobacter pylori strain 51

<400> SEQUENCE: 24

```
Met Lys Thr Phe Glu Ile Leu Lys His Leu Gln Ala Asp Ala Ile Val
  1               5                  10                  15

Leu Phe Met Lys Val His Asn Phe His Trp Asn Val Lys Gly Thr Asp
             20                  25                  30

Phe Phe Asn Val His Lys Ala Thr Glu Glu Ile Tyr Glu Gly Phe Ala
         35                  40                  45

Asp Met Phe Asp Asp Leu Ala Glu Arg Ile Val Gln Leu Gly His His
     50                  55                  60

Pro Leu Val Thr Leu Ser Glu Ala Leu Lys Leu Thr Arg Val Lys Glu
 65                  70                  75                  80

Glu Thr Lys Thr Ser Phe His Ser Lys Asp Ile Phe Lys Glu Ile Leu
                 85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
        130                 135                 140
```

<210> SEQ ID NO 25
<211> LENGTH: 144
<212> TYPE: PRT
<213> ORGANISM: Helicobacter pylori strain G27

<400> SEQUENCE: 25

```
Met Lys Thr Phe Glu Ile Leu Lys His Leu Gln Ala Asp Ala Ile Val
  1               5                  10                  15

Leu Phe Met Lys Val His Asn Phe His Trp Asn Val Lys Gly Thr Asp
             20                  25                  30

Phe Phe Asn Val His Lys Ala Thr Glu Glu Ile Tyr Glu Gly Phe Ala
         35                  40                  45

Asp Met Phe Asp Asp Leu Ala Glu Arg Ile Val Gln Leu Gly His His
     50                  55                  60

Pro Leu Val Thr Leu Ser Glu Ala Leu Lys Leu Thr Arg Val Lys Glu
 65                  70                  75                  80

Glu Thr Lys Thr Ser Phe His Ser Lys Asp Ile Phe Lys Glu Ile Leu
                 85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
        130                 135                 140
```

<210> SEQ ID NO 26
<211> LENGTH: 144
<212> TYPE: PRT
<213> ORGANISM: Helicobacter pylori strain Puno135

<400> SEQUENCE: 26

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
        35                  40                  45

Asp Met Phe Asp Asp Leu Ala Glu Arg Ile Val Gln Leu Gly His His
    50                  55                  60

Pro Leu Val Thr Leu Ser Glu Ala Ile Lys Leu Thr Arg Val Lys Glu
65                  70                  75                  80

Glu Thr Lys Thr Ser Phe His Ser Lys Asp Ile Phe Lys Glu Ile Leu
                85                  90                  95

Glu Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
    130                 135                 140

<210> SEQ ID NO 27
<211> LENGTH: 144
<212> TYPE: PRT
<213> ORGANISM: Helicobacter pylori strain NY40

<400> SEQUENCE: 27

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
        35                  40                  45

Asp Met Phe Asp Asp Leu Ala Glu Arg Ile Val Gln Leu Gly His His
    50                  55                  60

Pro Leu Val Thr Leu Ser Glu Ala Leu Lys Leu Thr Arg Val Lys Glu
65                  70                  75                  80

Glu Thr Lys Thr Ser Phe His Ser Lys Asp Ile Phe Lys Glu Ile Leu
                85                  90                  95

Gly Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Glu Ala His Leu Ala
    130                 135                 140

<210> SEQ ID NO 28
<211> LENGTH: 144
<212> TYPE: PRT
<213> ORGANISM: Helicobacter pylori strain P79

<400> SEQUENCE: 28

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

```
Phe Phe Asn Val His Lys Ala Thr Glu Glu Ile Tyr Glu Glu Phe Ala
            35                  40                  45

Asp Met Phe Asp Asp Leu Ala Glu Arg Ile Val Gln Leu Gly His His
    50                  55                  60

Pro Leu Val Thr Leu Ser Glu Ala Ile Lys Leu Thr Arg Val Lys Glu
 65                  70                  75                  80

Glu Thr Lys Thr Ser Phe His Ser Lys Asp Ile Phe Lys Glu Ile Leu
                85                  90                  95

Glu Asp Tyr Lys Tyr Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
    130                 135                 140

<210> SEQ ID NO 29
<211> LENGTH: 144
<212> TYPE: PRT
<213> ORGANISM: Helicobacter pylori strain Gambia94/24

<400> SEQUENCE: 29

Met Lys Thr Phe Glu Ile Leu Lys His Leu Gln Ala Asp Ala Ile Val
  1               5                  10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Gly Phe Ala
            35                  40                  45

Asp Met Phe Asp Asp Leu Ala Glu Arg Ile Val Gln Leu Gly His His
    50                  55                  60

Pro Leu Val Thr Leu Ser Glu Ala Leu Lys Leu Thr Arg Val Lys Glu
 65                  70                  75                  80

Glu Thr Lys Thr Ser Phe His Ser Lys Asp Ile Phe Lys Glu Ile Leu
                85                  90                  95

Gly Asp Tyr Lys His Leu Glu Lys Glu Phe Glu Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Glu Ala His Leu Ala
    130                 135                 140

<210> SEQ ID NO 30
<211> LENGTH: 144
<212> TYPE: PRT
<213> ORGANISM: Helicobacter pylori strain SouthAfrica7

<400> SEQUENCE: 30

Met Lys Thr Phe Glu Ile Leu Lys His Leu Gln Ala Asp Ala Ile Val
  1               5                  10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
            35                  40                  45

Asp Met Phe Asp Asp Leu Ala Glu Arg Ile Val Gln Leu Gly His His
    50                  55                  60

Pro Leu Val Thr Leu Ser Glu Ala Leu Lys Leu Thr Arg Val Lys Glu
 65                  70                  75                  80
```

```
Glu Thr Lys Thr Ser Phe His Ser Lys Asp Ile Phe Lys Glu Ile Leu
                85                  90              95

Gly Asp Tyr Lys His Leu Glu Lys Glu Phe Lys Glu Leu Ser Asn Thr
            100             105                 110

Ala Glu Lys Glu Asp Asp Lys Val Thr Val Thr Tyr Ala Asp Asp Arg
        115             120                 125

Leu Ala Lys Leu Gln Lys Ser Ile Trp Met Leu Glu Ala His Leu Ala
        130             135             140
```